United States Patent [19]
Jonckers et al.

[11] Patent Number: 6,118,023
[45] Date of Patent: Sep. 12, 2000

[54] METHOD FOR INCREASING THE CAPACITY OF AN EXISTING UREA PROCESS

[75] Inventors: Kees Jonckers, Susteren; Hendrik F. Perree, Waalre, both of Netherlands

[73] Assignee: DSM N.V., Heerlen, Netherlands

[21] Appl. No.: 09/005,224

[22] Filed: Jan. 9, 1998

[30] Foreign Application Priority Data

Jan. 13, 1997 [NL] Netherlands ............ 1004977

[51] Int. Cl.$^7$ .................................................. C07C 273/04
[52] U.S. Cl. .......................... 564/70; 564/66; 564/67; 564/69; 564/71; 564/72
[58] Field of Search .................. 564/66, 67, 69, 564/70, 71, 72

[56] References Cited

U.S. PATENT DOCUMENTS

| | | | |
|---|---|---|---|
| 3,356,723 | 12/1967 | Kaasenbrood | 564/67 |
| 3,936,500 | 2/1976 | Kaasenbrood | 564/67 |
| 4,504,679 | 3/1985 | Inoue et al. | 564/67 |
| 4,540,813 | 9/1985 | Van Nassau et al. | 564/71 |

FOREIGN PATENT DOCUMENTS 0 155 735  9/1985  European Pat. Off. .

OTHER PUBLICATIONS

Kirk–Othmer, Thyroid and Antithyroid Preparations to Vinyl Polymers, Encyclopedia of Chemical Technology, 3rd Ed., vol. 23, 1989.

DSM carbon dioxide stripping process, European Chemcial News Urea Supplement, Jan. 17, 1969.

*Primary Examiner*—Shailendra Kumar
*Attorney, Agent, or Firm*—Pillsbury Madison & Sutro LLP

[57] ABSTRACT

Method for increasing the capacity of an existing urea process, the existing urea process comprising a reactor (R), a pressure-reduction section (SC) and a urea-recovery section (U), characterized in that (i) a stripping column (S) is added, in which ammonium carbamate from the reaction mixture is stripped with carbon dioxide or is thermally stripped at almost the same elevated pressure, resulting in a gaseous mixture (G1) and a liquid mixture (M4), which liquid mixture (M4) is fed to the pressure-reduction section (SC), (ii) a condenser (C) is added, which is fed with the gaseous mixture (G1), ammonia and optionally carbon dioxide, in which the gaseous mixture (G1) is condensed at almost the same elevated reactor pressure (P) and at least 30% of the equilibrium amount of urea obtainable under the condensation conditions is furthermore formed, in which a liquid mixture containing urea, water and ammonium carbamate (MS) is formed, which mixture is fed to the bottom of the existing reactor (R), and a gaseous mixture (G2), and (iii) a scrubber (SCR) is added, in which the gaseous mixture (G2) is brought into contact with the aqueous ammoniacal ammonium carbamate solution (M3), in which a liquid (M6) mixture is obtained, which is fed to the condenser (C), and a scrubbed gaseous mixture (G3).

11 Claims, 4 Drawing Sheets

METHOD FOR INCREASING THE CAPACITY OF AN EXISTING UREA PROCESS

BACKGROUND OF THE INVENTION

The invention relates to a method for increasing the capacity of an existing urea process, the existing urea process comprising a process in which ammonia and carbon dioxide are fed to a reactor (R) at an elevated pressure (P) forming a reaction mixture (M1) comprising ammonium carbamate, ammonia, water and urea. The reaction mixture is then removed from the reactor and fed into a pressure-reduction section (SC) where the pressure is reduced, in either a single stage or in multiple stages, and heat is supplied to separate gaseous ammonia and ammonium carbamate from the reaction mixture to form a liquid mixture (M2). The gaseous ammonia and ammonium carbamate, once separated, are condensed and separated to obtain ammonia (M3') and an aqueous ammoniacal solution of ammonium carbamate (M3) and reused in forming a urea mixture (M2) from which urea is recovered in a urea-recovery section (U).

Such an existing urea process is described in Kirk-Othmer, Encyclopedia of Chemical Engineering, third edition, Volume 23, pages 553–556. In this publication such a process is described as the 'Solution-Recycle Process'. Examples of this process according to this publication are the so-called Mitsui-Toatsu Total Recycle C-Improved Process, the Montedison Urea Process and the UTI Heat-Recycle Process. This process for preparing urea is characterized in that ammonia and carbon dioxide are fed directly to a reactor. This process is furthermore characterized in that the excess ammonia and ammonium carbamate are separated from urea by reducing the pressure and simultaneously supplying heat. This in contrast to the so-called High-Pressure Gas-Stripping processes, such as the Stamicarbon $CO_2$ Stripping Process and the Snamprogretti $NH_3$ Stripping Process, in which the ammonium carbamate is recovered from the reaction mixture by stripping with ammonia, carbon dioxide or a different gas (at almost the same pressure as the pressure in the urea reactor), after which the gaseous mixture is condensed and returned to the reaction zone.

A method known to a person skilled in the art for substantially increasing the capacity of such 'Solution-Recycle Processes' is to replace equipment that constitutes a bottleneck in the process by larger apparatuses. Examples of equipment to be replaced are the urea reactor (R) and the intermediate pressure step (the first step) of the pressure-reduction section (SC). When these apparatuses are replaced by larger apparatuses the expensive high-pressure pumps for ammonia and ammonium carbamate will also often have to be replaced or added.

A drawback of the above method is that it is very expensive. This is partly caused by the high capital investment costs involved in replacing the urea reactor, the equipment for the intermediate pressure step, and the associated high-pressure pumps.

SUMMARY OF THE INVENTION

The aim of the present invention is to provide a method for substantially increasing the capacity of an existing 'Solution Recycle Process' type urea process, by eliminating or reducing the need for the replacement of expensive equipment.

This aim is achieved by the following modifications:

(i) adding a stripping column (S) for stripping the ammonium carbamate from the reaction mixture (M1) with either carbon dioxide or heat without substantially reducing the pressure below the pressure (P) of the reactor (R), resulting in a gaseous mixture (G1) and a liquid mixture (M4), the liquid mixture (M4) then being fed into the pressure-reduction section (SC);

(ii) adding a condenser (C), into which is fed the gaseous mixture (G1), ammonia, and optionally carbon dioxide, in which the gaseous mixture (G1) is condensed without substantially reducing the pressure below the pressure (P) of the reactor (R) to form a liquid mixture (M5) that contains urea, water, and ammonium carbamate, the urea content being at least 30% of the equilibrium amount of urea obtainable under the condensation conditions, and a gaseous mixture (G2), with the liquid mixture (M5) being returned to the bottom of the reactor (R); and (iii) adding a scrubber (SCR), in which the gaseous mixture (G2) is brought into contact with the aqueous ammoniacal ammonium carbamate solution (M3), to form a liquid mixture (M6) which is then fed to the condenser (C), and a scrubbed gaseous mixture (G3).

It has been found that when the method according to the invention is used, a greater urea capacity can be obtained using the same urea reactor (R). A further advantage is that under certain conditions, replacing the intermediate pressure step of the existing plant will be unnecessary. Similarly, in a preferred embodiment of the invention, the existing high-pressure ammonia and high-pressure ammonium carbamate pumps need not be replaced. It has been found that applying the invention can triple the urea capacity of an existing urea process.

An important additional advantage is that the amount of steam per ton of urea produced is lower than in the existing process. It has been found that the energy load can be reduced by at least 500 kg of high-pressure steam per ton of urea.

FIG. 1 schematically represents processes whose urea capacity can be increased by the present invention.

FIG. 2 schematically shows an example of an urea process modified in accordance with the present invention.

Urea processes whose urea capacity can be advantageously increased by the present invention are, for example, the aforementioned Mitsui-Toatsu Total Recycle C-Improved Process, the Montedison Urea Process, the UTI Heat-Recycle Process, the conventional Stamicarbon process, and the Chemico process. These processes are characterized by (and are schematically represented in FIG. 1, in which the following symbols have been used):

(a) a reaction zone in which ammonia and carbon dioxide are fed to a reactor (R) at a pressure between 18 and 30 MPa and a temperature between 180 and 220° C.;

(b) a pressure-reduction section (SC), usually consisting of two or more steps in which the pressure is reduced with simultaneous supply of heat (steam) that may include an intermediate pressure step in which the pressure is reduced to 1.5 to 8.0 MPa and a low pressure step in which the pressure is reduced to 0.2 to 1.0 MPa, with the gaseous mixture produced subsequently condensed to form an aqueous ammonium carbamate solution (M3) and a liquid ammonia stream (M3'), which is returned to the urea reactor (R); and (c) an urea-recovery section (U) in which urea is recovered, water is separated and ammonium carbamate is obtained with the ammonium carbamate (M3) being returned to the reaction zone (optionally via the condensers of the pressure-reduction section (SC)).

The urea-recovery section (U) may have different designs for the different embodiments of the 'Solution Recycle Processes'. Reference is made to the aforementioned encyclopedia. It has been found, however, that the advantages of the present invention do not depend upon the actual design of the urea recovery section (U).

DETAILED DESCRIPTION OF THE INVENTION

Figure 2:
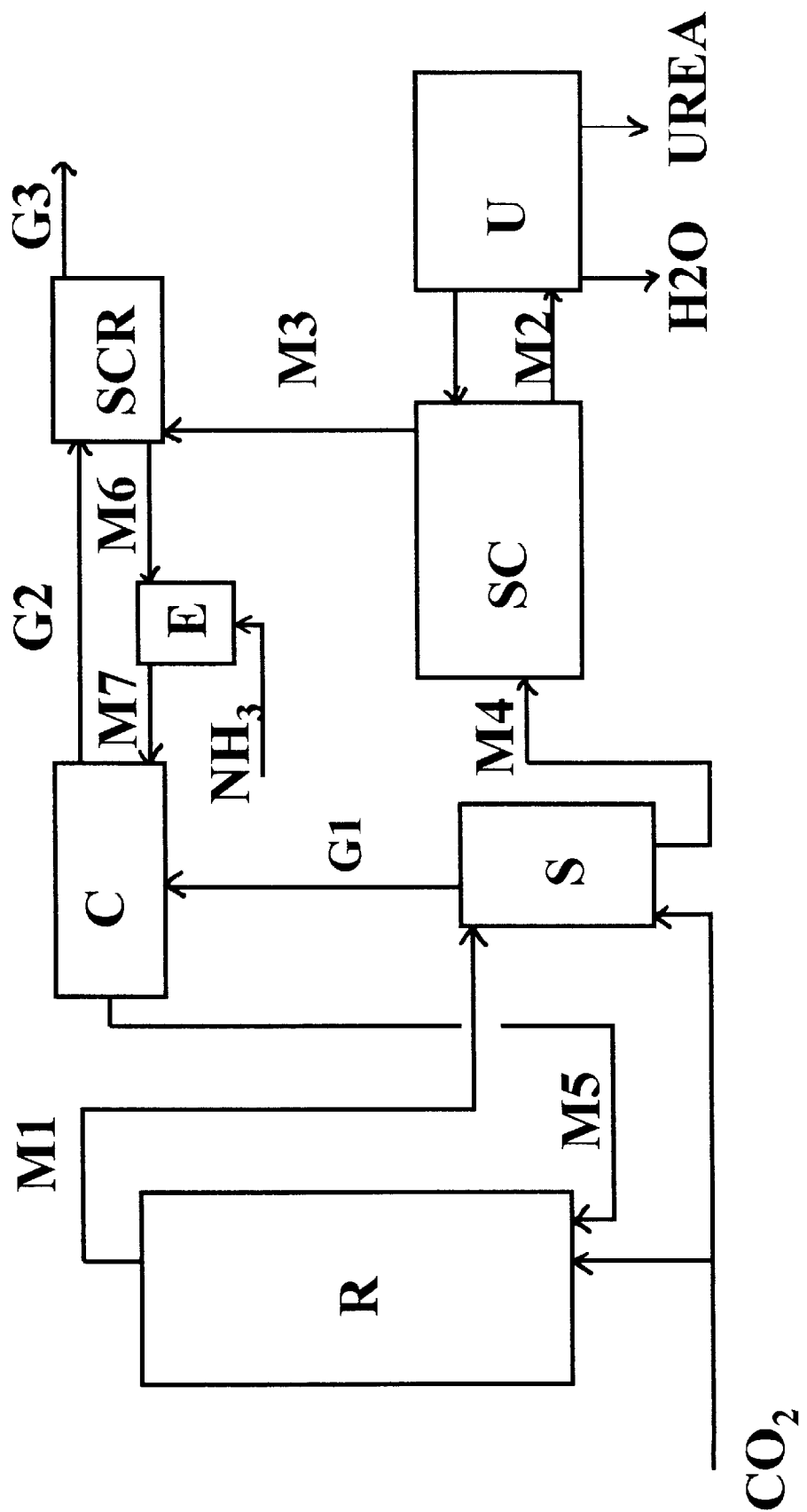
FIG. 2 is a schematic representation of a convention urea process modified according to the present invention.

An example of an urea process modified in accordance with the present invention is schematically represented in FIG. 2, in which the symbols used below are indicated. For simplicity, FIG. 2 includes no steam streams.

The stripping column (S) and the way in which it can be operated are generally known to a person skilled in the art and are described, for example, in U.S. Pat. No. 3,356,723 with respect to carbon dioxide. 'Thermal stripping' is used herein to describe the thermal decomposition of ammonium carbamate and the removal of the carbon dioxide and ammonia formed from the solution (M1). Thermal stripping, for example, is included in the Snamprogetti NH$_3$ stripping process as described on pages 559–562 of the aforementioned Encyclopedia. Preferably, however, carbon dioxide is used as the stripping gas to achieve greater stripping efficiency. The stripping column is fitted with means for supplying heat. Usually the stripping column is designed as a vertical column containing vertical tubes in which the stripping process takes place, the tubes being heated with steam on the shell side. This steam preferably has a pressure of between 1.5 and 4.0 MPa. The stripping gas is fed to the bottom of the stripping column and the reactor effluent, reaction mixture (M1), is fed to the top. The gaseous mixture (G1) is recovered at the top of the stripping column (S). The gaseous mixture recovered consists substantially of ammonia and carbon dioxide. At the bottom of the stripping column (S) a mixture (M4) is recovered that consists substantially of urea, water and a residual amount of ammonium carbamate.

The pressure at which the stripping takes place is almost equal to the pressure in the urea reactor (R). These pressures may differ somewhat as a function of differences in the vertical positioning of the process equipment. If carbon dioxide is used as the stripping gas, the differences in pressure will, for example, generally be less than 0.3 MPa.

The gaseous mixture (G1) is condensed in the condenser (C), resulting in the formation of ammonium carbamate. The aqueous ammoniacal solution (M6) is fed to the condenser together with ammonia. By ensuring sufficient residence time, typically 10–30 minutes, in the condenser, at least 30%, and preferably 50–80%, of the equilibrium amount of urea obtainable under the condensation conditions can be formed. It has been found that the so-called N/C ratio is important for obtaining optimum urea yields. The N/C ratio is defined as follows:

$$N/C = \frac{2*\text{moles urea} + \text{moles NH}_3}{\text{moles urea} + \text{moles CO}_2}$$

where moles NH$_3$ equals the free ammonia plus the ammonia bound in ammonium carbamate and moles CO$_2$ equals the free carbon dioxide plus the carbon dioxide bound in the ammonium carbamate. Preferably the N/C ratio lies between 2.7 and 4.0, more preferably between 2.8 and 3.5. The N/C ratio can be adjusted by setting the carbon dioxide and ammonia feeds. If carbon dioxide is used as the stripping gas, the carbon dioxide feed equals or almost equals the amount of carbon dioxide used as the stripping gas. The ammonia feed is the amount of ammonia that is fed to the condenser.

The condenser (C) is preferably designed as a so-called submerged condenser, with the gas mixture to be condensed being fed into the shell area of a shell-and-tube heat exchanger as, for example, described in NL-A-8400839. A liquid level in the heat exchanger can be simply obtained by means of an overflow partition. The heat of dissolution and condensation released is discharged with the aid of a medium flowing through tubes, for example water, which in the process is converted into low-pressure steam, or with the liquid mixture (M4) obtained in the stripping column. The submerged condenser may be arranged horizontally or vertically.

It is particularly advantageous to carry out the condensation in a horizontally arranged submerged condenser. Preferably the condenser is placed higher or at the same level as the top of the urea reactor (R). This provides the advantage that the mixture (M5) leaving the condenser (C) can be fed to the reactor (R) under the influence of gravity.

With the method according to the invention, the temperature in the condensation zone can be increased by 5–10° C., depending on the pressure applied (P) and the amount of urea and water formed. In this way it is possible, for example by appropriately sizing the heat-exchanging area, to generate low-pressure steam of 0.5–1 MPa at condenser pressures of approximately 16 MPa. It is, of course, also possible to obtain low-pressure steam at the more typical pressure of 0.3–0.5 MPa by using a substantially smaller heat-exchanging area.

Ammonia, and optionally carbon dioxide, are also added to the condenser (C). Carbon dioxide is added if thermal stripping is carried out in the stripping column. It is advantageous to feed these gases to the condenser in a manner that ensures thorough mixing with the reaction mixture. Preferably the gases are introduced at the bottom of the reaction mixture and over the entire length of a horizontal condenser.

Because it is not possible, due to equilibrium conditions, to condense all the gaseous components in the condenser (C) a portion of the gas mixture (G2) has to be discharged. In addition to inert gases, this gas mixture (G2) also contains carbon dioxide and ammonia, both of which are preferably returned to the process. By bringing this gas mixture into contact with the aqueous ammoniacal solution of ammonium carbamate (M3) in the scrubber (SCR), an amount of these valuable gases can be recovered. The liquid mixture (M6) that has absorbed a portion of the ammonia and carbon dioxide leaves the scrubber and is fed to the reaction mixture in the condenser (C). Preferably ammonia is used to drive an ejector (E) so that the mixture (M6) is drawn in. The liquid mixture (M7) of ammonia and ammonium carbamate thus obtained is subsequently fed to the condenser (C) as described above. It has also been found that it is advantageous to place the scrubber inside the condenser's pressure vessel. The provisions for operating the scrubber at the elevated pressure (P) are consequently less extreme, which leads to a significant cost advantages.

Figure 3A:
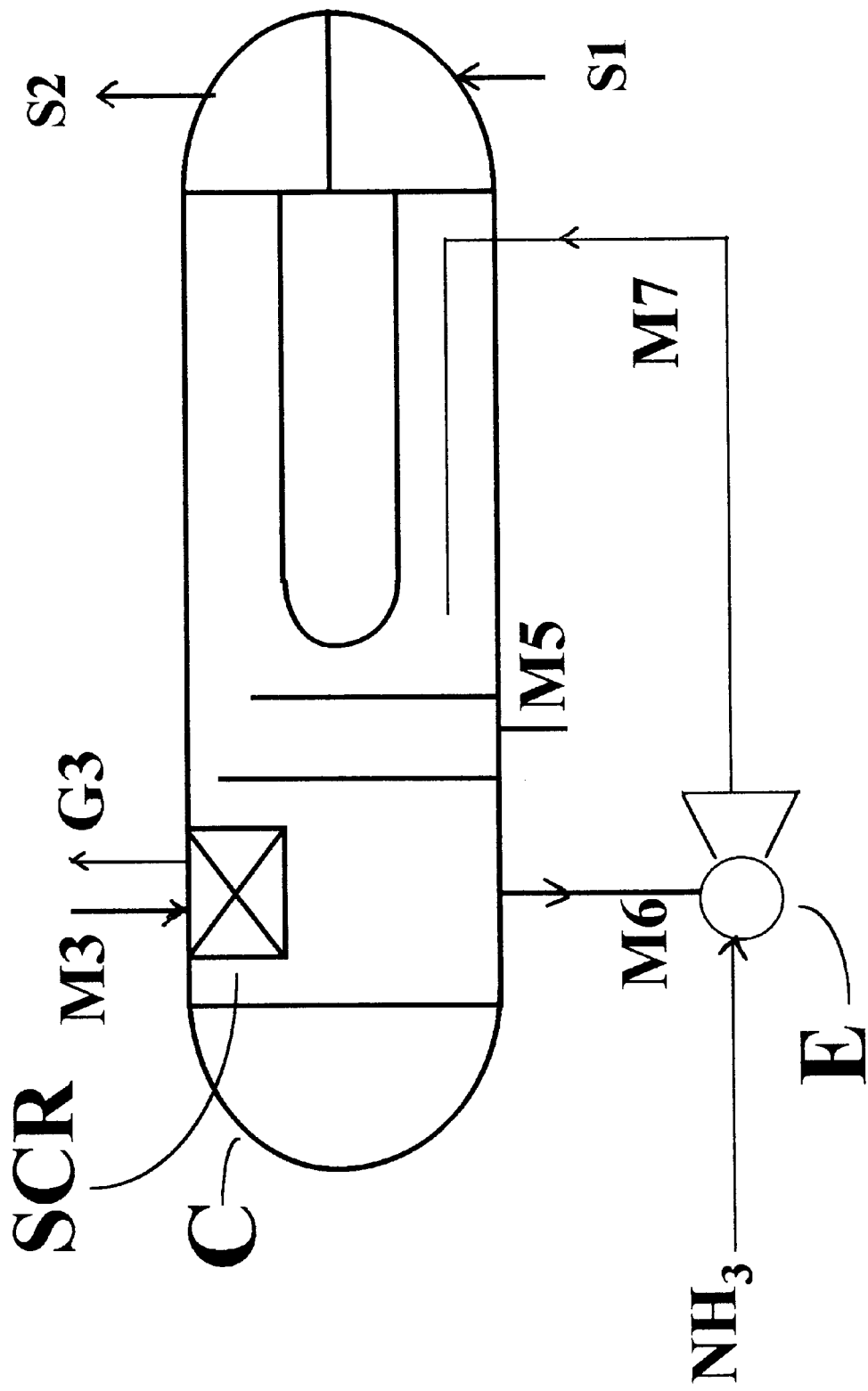
FIGS. 3a and 3b are schematic representations of horizontally configured ammonium carbamate condensers that may be utilized in conjunction with the present invention.
Figure 3B:
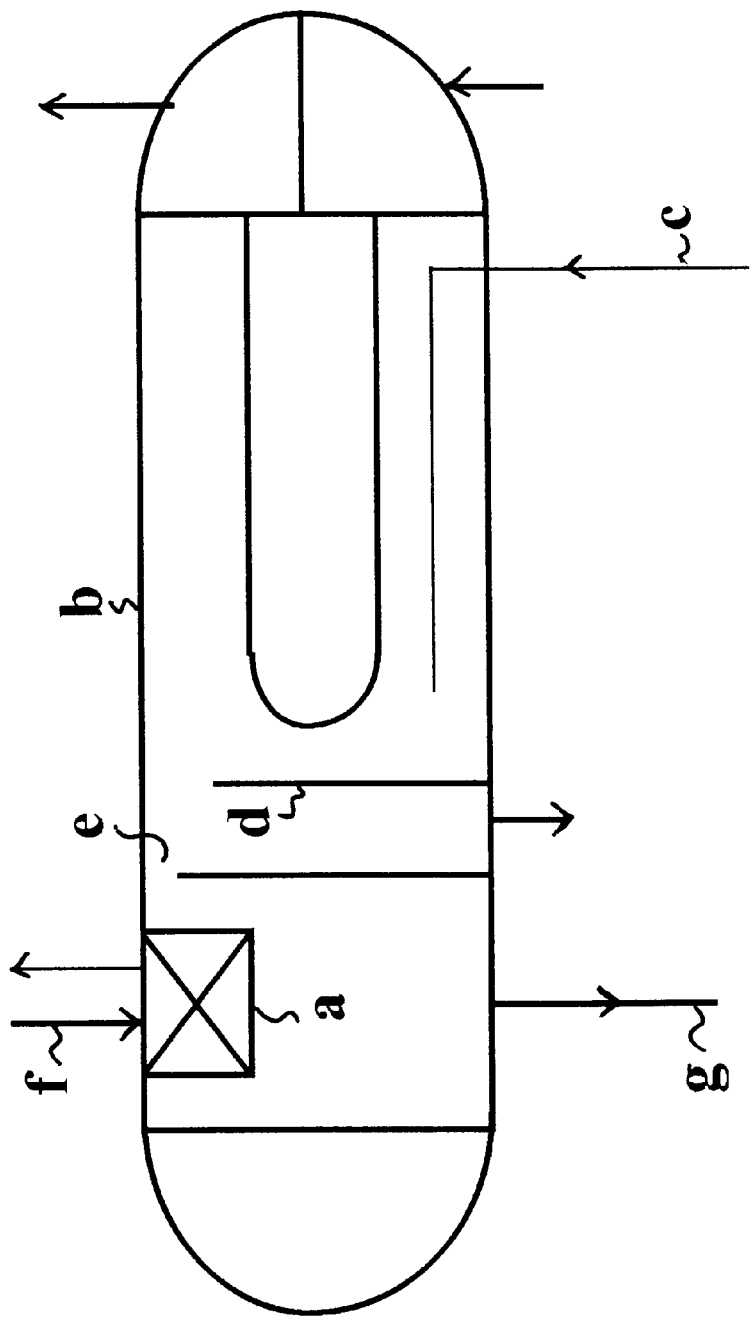

The invention also relates to the condenser described above, in which the scrubber has been placed inside the condenser's pressure shell. As shown in FIG. 3b, such a condenser is designed as a horizontal submerged condenser with a scrubber (a) placed inside the condenser's pressure shell (b), the condenser being fitted with means (c) for feeding a stream to the bottom of the shell side of the condenser, means (d) that ensure a sufficient liquid level and liquid residence time in the condenser, means (e) that ensure that the gas above the liquid level can leave the condenser via the scrubber, means (f) that ensure that a liquid feed can be fed to the scrubber and means (g) for discharging the liquid mixture from the scrubber from the condenser. Such a condenser (C) according to the invention is schematically represented in FIG. 3a, in which the scrubber (SCR) has been placed inside the condenser's pressure vessel. In FIG. 3a (S1) represents the boiler feed water and (S2) the steam obtained.

The urea reactor (R) does not have to be replaced in the present invention. In accordance with the modified arrangement of the equipment provided by the present invention, certain adjustments in the way in which the reactor is operated will be necessary and certain others preferable. The reactor will be fed with an aqueous solution of ammonium carbonate as before (old; (M3), new: (M5)). The composition of the new feed stream, mixture (M5), differs from the old feed stream, mixture (M3), in that it additionally contains a large amount of urea formed in the condenser (C). In the reactor the ammonium carbamate is converted into urea and water. The energy required for this reaction can be supplied by feeding a hot gas into the bottom of the reactor. This hot gas may be for example ammonia, carbon dioxide, or a portion of the gaseous mixture (G1) from the stripper (S). Preferably carbon dioxide is used for this purpose. In a preferred embodiment a portion of the hot, pressurized carbon dioxide feed is passed to the bottom of the reactor (R) and the remainder is passed to the stripping column (S) to serve as the stripping gas. The provisions already present for feeding carbon dioxide can be advantageously used for feeding the carbon dioxide to the reactor (R). The ratio of the carbon dioxide that is fed directly to the reactor and the amount that is fed to the stripper is preferably between 1:5 and 1:20.

Because a portion of the urea has already been formed in the condenser, the equilibrium position in the reaction mixture (M1) can be maintained while, for example, tripling the urea production capacity relative to the production capacity of the unimproved process. Moreover, with a stripping column (S) installed, it is found that degrees of both carbon dioxide and ammonia conversion of 70–80% can be realized in mixture (M4), whereas in the original process, the degree of carbon dioxide conversion generally lies at approximately 65% and the degree of ammonia conversion at approximately 40%. The degree of carbon dioxide conversion and the degree of ammonia conversion are defined as follows:

$$\text{Degree of carbon dioxide conversion} = \frac{\text{moles urea}}{\text{moles urea} + \text{moles CO}_2}$$

where moles $CO_2$ equals the molar amount of free carbon dioxide plus the carbon dioxide bound in ammonium carbamate and $$\text{Degree of ammonia conversion} = \frac{2 * \text{moles urea}}{2 * \text{moles urea} + \text{moles NH}_3}$$

where moles $NH_3$ equals the molar amount of free ammonia plus the ammonia bound in ammonium carbamate.

Because mixture (M4) contains more urea and less ammonia and carbon dioxide than mixture (M1) of the old process, less energy will be required per ton of urea to separate these components in the pressure-reduction section (SC). This advantage holds for the so-called intermediate pressure step in particular. This means that when use is made of the existing equipment of the pressure-reduction section (SC), and in particular the intermediate pressure step, more urea can be produced with this installation. The fact that mixture (M4) contains comparatively less ammonia and carbon dioxide also means that less ammonium carbamate per tone of urea produced is returned via (M3). This results in extra capacity of the existing high-pressure ammonium carbamate pumps which pump the mixture (M3) back to the condenser (C). This extra capacity can also be used to increase the existing installation's urea capacity.

The increased degrees of ammonia and carbon dioxide conversion and the reduction of the N/C ratio (in comparison with the original process) eliminate the need for ammonia return stream (M3'). The resulting extra capacity of the high-pressure ammonia pump (in FIG. 1 the pump that pumps $NH_3$ and M3') can be dedicated to supplying the extra ammonia required to support the increased urea production capacity provided by improved process of the present invention.

As a result of the installation of a stripping column it is advantageous to operate the reactor under the following conditions. There is an optimum pressure (P) at which the degree of conversion to urea and the efficiency of the stripper are optimum. The pressure is preferably 15–18 MPa. The temperature will depend on the chosen pressure, and will lie between 180 and 190° C.

The invention will be elucidated with reference to the following non-limiting example.

EXAMPLE

Figure 1:
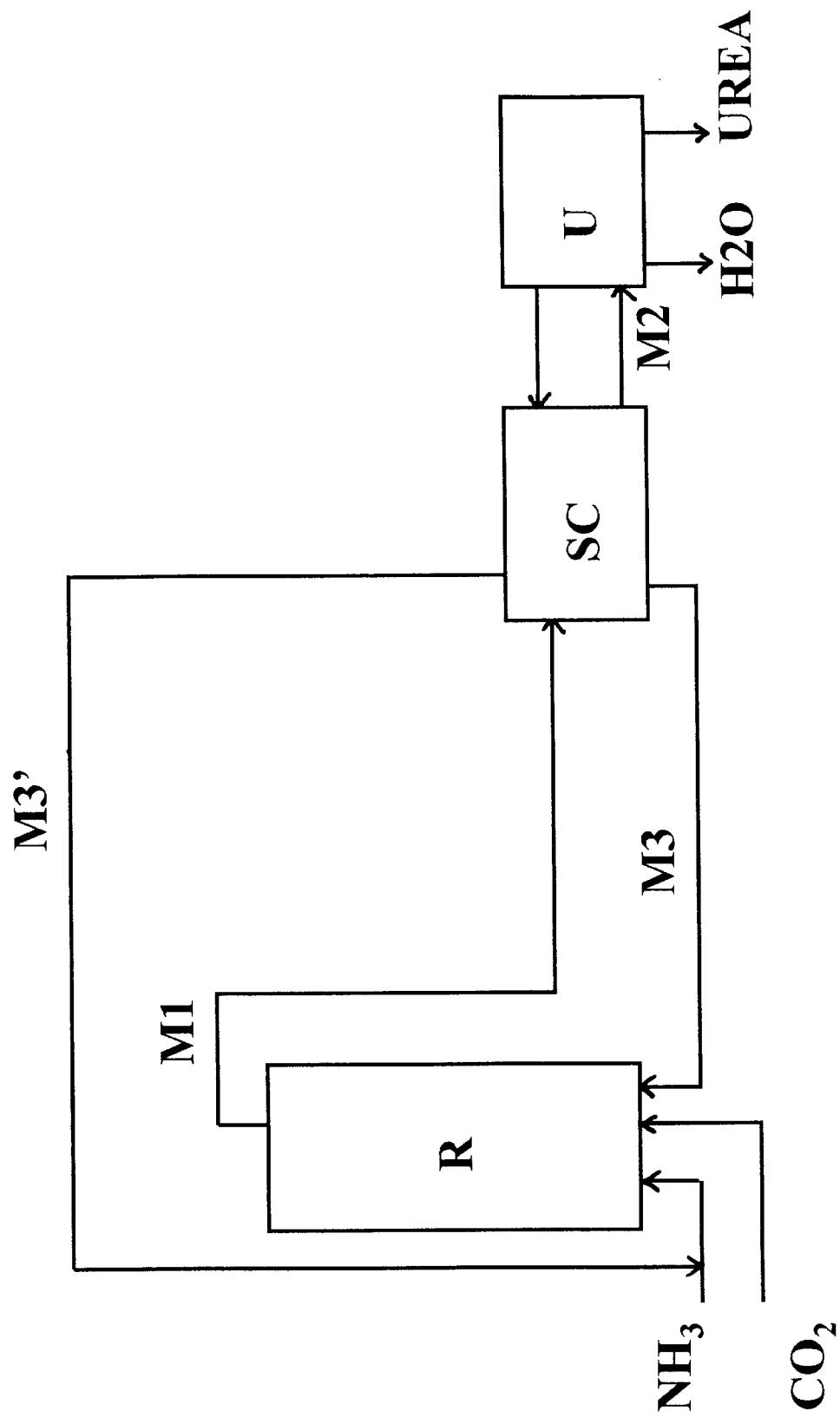
FIG. 1 is a schematic representation of conventional urea processes.

A urea process as schematically represented in FIG. 1 is adjusted according to the invention, resulting in the process schematically represented in FIG. 2.

The existing process comprised a reactor (R) with a volume of 55 m³. The pressure and temperature in the old process were 20 MPa and 190° C. The degree of carbon dioxide conversion based on the composition of mixture (M1) was 64% and the degree of ammonia conversion was 32%. The existing installation's overall urea capacity was 550 metric tones of urea per day. The energy consumption of this installation can be expressed in 1500 kg of steam (1.3 MPa) per ton of urea produced. The heat stream required in the intermediate pressure step (part of pressure-reduction section (SC)) of this installation at this capacity was 11 million kcal/h.

A few flow rates of different streams are indicated below by way of illustration:

| STREAM (see FIG. 1) | (Kg/hr) |
|---|---|
| $CO_2$ | 16,900 |
| $NH_3$ | 30,900 |
| M1 | 77,400 |
| M3 | 29,600 |
| urea | 22,900 |

In the adjusted process (FIG. 2) the existing reactor and the intermediate pressure step of the pressure-reduction section (SC) have been maintained. Attempts were made to increase the urea capacity by using the existing reactor, with the limitation that the heat stream in the intermediate pressure step could not exceed 11 million kcal/h (see above). It was found that the capacity could be increased to 1650 metric tones of urea per day by placing the stripping column, the condenser, and the scrubber according to the present invention. The pressure (P) in the reactor, stripper, and condenser was 16 MPa and the reactor temperature was 187° C. The N/C ratio in the condenser was 3.3. The energy consumption of the new installation was 1003 kg of steam (about half of which was steam of 1.3 MPa and the other half steam of 2.5 MPa) per ton of urea produced. This also resulted in a surplus of approximately 10 tons/h of 0.53 MPa steam, which can be used elsewhere. The degree of carbon dioxide conversion based on the composition of mixture (M4) was 68% and the degree of ammonia conversion in the same mixture was 65%.

A few flow rates of different streams are indicated below by way of illustration:

| STREAM (See FIG. 2) | (Kg/hr) |
|---|---|
| $CO_2$ (to reactor) | 4,700 |
| $CO_2$ (to stripper) | 46,000 |
| $NH_3$ | 39,300 |
| M3 | 62,700 |
| M4 | 149,800 |
| urea | 68,750 |

As is apparent from the above figures, it is possible to increase the urea capacity by a factor of 3 and to reduce the amount of energy consumed per ton of urea. This while existing expensive equipment such as the reactor and the intermediate pressure step can be maintained. The spare pump of the original process can be advantageously used for the higher flow rate of (M3).

We claim:

1. A method for increasing the capacity of an existing urea process, the existing urea process comprising a process in which ammonia and carbon dioxide are fed to a reactor (R) at an elevated pressure (P), in which a reaction mixture (M1) comprising ammonium carbamate, ammonia, water and urea is prepared, after which, by reducing the pressure once or several times and supplying heat, gaseous ammonia and ammonium carbamate are separated from the reaction mixture in a pressure-reduction section (SC), which reaction mixture results in a liquid mixture (M2) and the gaseous ammonia and ammonium carbamate thus recovered are condensed, in which ammonia (M3') is separated and an aqueous ammoniacal solution of ammonium carbamate (M3) is obtained, which solution (M3) and the ammonia obtained (M3') are reused to prepare urea and in which urea is recovered from the mixture (M2) in a urea-recovery section (U), characterized in that (i) a stripping column (S) is added, in which ammonium carbamate from the reaction mixture (M1) is stripped with carbon dioxide or is thermally stripped at almost the same elevated pressure (P), resulting in a gaseous mixture (G1) and a liquid mixture (M4), which liquid mixture (M4) is fed to the pressure-reduction section (SC), (ii) a condenser (C) is added, which is fed with the gaseous mixture (G1), ammonia and optionally carbon dioxide, in which the gaseous mixture (G1) is condensed at almost the same elevated pressure (P) and at least 30% of the equilibrium amount of urea obtainable under the condensation conditions is furthermore formed, in which a liquid mixture containing urea, water and ammonium carbamate (M5) is formed, which mixture is fed to the bottom of the existing reactor (R), and a gaseous mixture (G2), and (iii) a scrubber (SCR) is added, in which the gaseous mixture (G2) is brought into contact with the aqueous ammoniacal ammonium carbamate solution (M3), in which a liquid (M6) mixture is obtained, which is fed to the condenser (C), and a scrubbed gaseous mixture (G3).

2. Method according to claim 1, characterized in that between 50 and 80% of the equilibrium amount of urea obtainable under the condensation conditions is formed in the condenser.

3. Method according to claim 2, characterized in that the residence time in condenser (C) is 10–30 minutes.

4. Method according to any one of claims 1–3, characterized in that the condenser (C) is a submerged condenser.

5. Method according to claim 4, characterized in that the condensation is carried out on the shell side of a horizontally arranged shell-and-tube heat exchanger.

6. Method according to claim 5, characterized in that the scrubber (SCR) has been placed inside the pressure vessel of the condenser (C).

7. A method according to claim 2, wherein the condenser (C) is positioned above the reactor (R) in the existing process.

8. A method according to claim 1, wherein the stripping gas used in stripping column (S) is carbon dioxide.

9. A method according to claim 8, wherein carbon dioxide is also fed to the bottom of reactor (R) and further wherein the ratio of carbon dioxide fed into the reactor and the carbon dioxide fed into the stripping column (S) is at least 1:5.

10. A method according to any one of claims 1–3, 7 or 9, characterized in that the pressure in reactor (R) of the new process is between 15 and 18 MPa.

11. A method according to any one of claims 2 or 9, wherein the N/C ratio in the condenser (C) and reactor (R) of the new process is between 2.8 and 3.5.

* * * * *